(12) United States Patent
Shih et al.

(10) Patent No.: US 12,023,397 B2
(45) Date of Patent: Jul. 2, 2024

(54) SCALP PROTECTION COMPOSITION

(71) Applicant: PATECH FINE CHEMICALS CO., LTD., Taipei (TW)

(72) Inventors: Hou-Kuang Shih, Xianxi Township, Changhua County (TW); Jung-Tsung Hung, Xianxi Township, Changhua County (TW); Hsu-Hua Tang, Xianxi Township, Changhua County (TW); Yu-Kai Chen, Xianxi Township, Changhua County (TW); An-Hung Liang, Xianxi Township, Changhua County (TW); Jeng-Shiang Tsaih, Xianxi Township, Changhua County (TW)

(73) Assignee: PATECH FINE CHEMICALS CO., LTD., Taipei (TW)

( * ) Notice: Subject to any disclaimer, the term of this patent is extended or adjusted under 35 U.S.C. 154(b) by 0 days.

(21) Appl. No.: 17/832,918

(22) Filed: Jun. 6, 2022

(65) Prior Publication Data
US 2022/0409505 A1   Dec. 29, 2022

(30) Foreign Application Priority Data

Jun. 11, 2021 (TW) .................... 110121484

(51) Int. Cl.
*A61K 8/37*   (2006.01)
*A61K 8/06*   (2006.01)
*A61Q 17/00*  (2006.01)

(52) U.S. Cl.
CPC ............. *A61K 8/37* (2013.01); *A61K 8/062* (2013.01); *A61Q 17/00* (2013.01)

(58) Field of Classification Search
CPC .................. A61K 8/37; A61Q 5/002
See application file for complete search history.

(56) References Cited

U.S. PATENT DOCUMENTS

2019/0201305 A1*   7/2019   Nakano ............... A61K 8/345

FOREIGN PATENT DOCUMENTS

| CN | 111991273 A | * 11/2020 | ........... A61K 8/0295 |
| JP | 2005306786 A | * 11/2005 | |

OTHER PUBLICATIONS

JP-2005306786-A (Espacenet English translation, downloaded May 2023) (Year: 2023).*
CN-111991273-A (Espacenet English translation, downloaded May 2023) (Year: 2023).*

\* cited by examiner

*Primary Examiner* — Mark V Stevens
(74) *Attorney, Agent, or Firm* — HSML P.C.

(57) ABSTRACT

Disclosed herein is a scalp protection composition that includes a carboxylate compound, an emulsifier, and water. The carboxylate compound is represented by formula (I):

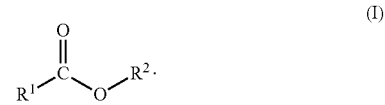

In formula (I), $R^1$ represents a $C_4$-$C_8$ alkyl group, and $R^2$ represents a $C_{10}$-$C_{26}$ alkyl group.

5 Claims, No Drawings

SCALP PROTECTION COMPOSITION

CROSS-REFERENCE TO RELATED APPLICATION

This application claims priority of Taiwanese Invention Patent Application No. 110121484, filed on Jun. 11, 2021.

FIELD

The present disclosure relates to a scalp protection composition, and more particularly to a scalp protection composition which can protect the scalp from damages caused by hair dyes and perm agents.

BACKGROUND

Most of the commercially available hair products (such as hair dyes and perm agents) are strong alkaline substances with a pH value ranging from 8.0 to 14.0. When the user's scalp comes into contact with these hair products, the scalp might be damaged, and causes irritation, redness, itching, etc. Therefore, before applying hair dyes and perm agents to the hair, a scalp protectant needs to be applied to the scalp in order to isolate and avoid direct contact of the hair dyes and perm agents with the scalp.

At present, the strong alkali-resistant dimethicone or mineral oil contained in the scalp protectants can isolate the scalp from hair dyes and perm agents and achieve the effect of protecting the scalp.

In spite of the aforesaid, there is still a need for those skilled in the art to develop a scalp protection composition having excellent hydrolysis resistance, moisture retention, and spreadability, so as to meet industrial requirements.

SUMMARY

Therefore, an object of the present disclosure is to provide a scalp protection composition that can alleviate at least one of the drawbacks of the prior art.

The scalp protection composition includes a carboxylate compound, an emulsifier, and water. The carboxylate compound is represented by formula (I):

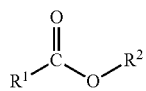

(I)

wherein:
$R^1$ represents a $C_4$-$C_8$ alkyl group; and
$R^2$ represents a $C_{10}$-$C_{26}$ alkyl group.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a scalp protection composition including a carboxylate compound, an emulsifier, and water. The carboxylate compound is represented by formula (I):

(I)

wherein:
$R^1$ represents a $C_4$-$C_8$ alkyl group; and
$R^2$ represents a $C_{10}$-$C_{26}$ alkyl group.

According to the present disclosure, the scalp protection composition can protect the scalp from damages caused by hair products.

As used herein, the term "hair product" refers to any hair product with strong alkalinity, such as hair dyes and perm agents.

According to the present disclosure, the scalp protection composition is suitable for application to the scalp before hair coloring or perming to protect the scalp.

In certain embodiments, $R^1$ represents a $C_4$-$C_8$ branched chain alkyl group, thereby enabling the scalp protection composition to have better hydrolysis resistance to alkaline hair dyes and perm agents. In other embodiments, $R^1$ represents a branched chain alkyl group that has a total carbon number of $C_4$ to $C_8$, and at least one hydrogen on the α-carbon or β-carbon is substituted with an alkyl group.

In certain embodiments, $R^2$ represents a $C_{10}$-$C_{26}$ branched chain alkyl group, thereby enabling the scalp protection composition to have better hydrolysis resistance to alkaline hair dyes and perm agents.

In certain embodiments, the carboxylate compound may be selected from the group consisting of:
(1) a compound represented by formula (I-1) (i.e., 2-octyldodecyl 2-ethylhexanoate, CAS No. 69275-04-3):

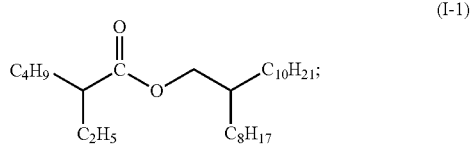

(I-1)

(2) a compound represented by formula (I-2):

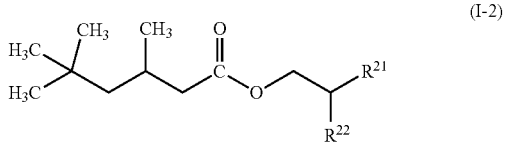

(I-2)

wherein in formula (I-2), $R^{21}$ represents a $C_1$-$C_{11}$ straight chain or branched chain alkyl group, and $R^{22}$ represents a $C_{12}$-$C_{13}$ straight chain or branched chain alkyl group; and (3) a compound represented by formula (I-3):

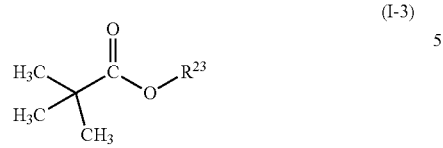

(I-3)

wherein in formula (I-3), $R^{23}$ represents a $C_{10}$ branched chain alkyl group. The $C_{10}$ branched chain alkyl group may be an isodecyl group and branched chain isomers thereof.

According to the present disclosure, the procedures and conditions for synthesizing the carboxylate compound are within the expertise and routine skills of those skilled in the art. Examples of the method for synthesizing the carboxylate compound may include, but are not limited to, esterification of $R^1$—COOH and $R^2$—OH in the absence of a catalyst, or esterification of $R^1$—COOH and $R^2$—OH in the presence of a catalyst.

Examples of the catalyst may include, but are not limited to, stannous oxalate, stannous oxide, tetrabutyl titanate, titanium tetraisopropanolate, and methanesulfonic acid.

In certain embodiments, the carboxylate compound may be present in an amount ranging from 0.5 wt % to 99 wt %, based on the total weight of the scalp protection composition, so that the scalp protection composition can be evenly applied to the scalp, thereby completely protecting the scalp from alkaline hair products.

In certain embodiments, the emulsifier may be selected from the group consisting of fatty acid salt, sulfonate, amino acid salt, alkyl ether sulfate, alkyl sulfonate, sucrose ester, alkyl polyglucoside, glycerol ester, polyglycerol ester, sorbitan ester, polysorbate, fatty acid diethanolamide, fatty alcohol polyoxyethylene ether, fatty alcohol polyalkylene glycol ether, alkyl amide betaine, alkyl betaine, alkyl ammonium chloride, and combinations thereof.

In certain embodiments, the emulsifier may be present in an amount ranging from 0.5 wt % to 50 wt %, based on the total weight of the scalp protection composition.

In certain embodiments, the water may be present in an amount ranging from 0.5 wt % to 99 wt %, based on the total weight of the scalp protection composition.

According to the present disclosure, the scalp protection composition may be formulated into a dosage form suitable for use on the scalp using technology well known to those skilled in the art. Examples of the suitable dosage form include, but are not limited to, oil-in-water (O/W) type, water-in-oil (W/O) type, water-in oil-in water (W/O/W) type or oil-in water-in oil (O/W/O) type emulsions, or gels, creams, liniments, sprays, foams, dispersions, drops, and mousses.

According to the present disclosure, in order to achieve the effect of protecting the scalp, the scalp protection composition can be applied evenly to the scalp prior to application of alkaline hair dyes and perm agents. The scalp protection composition has good hydrolysis resistance to alkaline hair products, so it is not easily hydrolyzed by alkaline hair products and can stably cover the scalp, thereby effectively separating the scalp from the alkaline hair products.

The disclosure will be further described by way of the following examples. However, it should be understood that the following examples are solely intended for the purpose of illustration and should not be construed as limiting the disclosure in practice.

Synthesis Example 1: Carboxylate Compound of Formula (I-1)

269±5% g of 2-ethylhexanoic acid (CAS No. 149-57-5) was mixed with 562±5% g of 2-octyl-1-dodecanol (CAS No. 5333-42-6) in a reactor, and the resultant mixture was subjected to an esterification reaction at 220° C. in the presence of a catalyst, so as to obtain an esterified product. Next, the esterified product was subjected to cooling, removal of the catalyst and unreacted 2-ethylhexanoic acid, decolorization, and deodorization in sequence, so as to obtain a carboxylate compound of formula (I-1).

Synthesis Example 2: Carboxylate Compound of Formula (I-2)

248±5% g of 3,5,5-tnmethylhexanoic acid (CAS No. 3302-10-1) was mixed with 579±5% g of ISOFOL 2426S (which contained $C_{24}$-$C_{26}$ branched chain alkyl alcohols and purchased from Sasol Co., Ltd.) in a reactor, and the resultant mixture was subjected to an esterification reaction at 220° C. in the presence of a catalyst, so as to obtain an esterified product. Next, the esterified product was subjected to cooling, removal of the catalyst and unreacted 3,5,5-tnmethylhexanoic acid, decolorization, and deodorization in sequence, so as to obtain a carboxylate compound of formula (I-2).

Synthesis Example 3: Carboxylate Compound of Formula (I-3)

337±5% g of neopentanoic acid (CAS No. 75-98-9) was mixed with 522±5% g of a $C_{10}$ branched chain alkyl alcohol (which contained isodecyl alcohol and branched chain isomers thereof) (purchased from ExxonMobil Corp.; Cat. No. EXXAL 10) in a reactor, and the resultant mixture was subjected to an esterification reaction at 220° C. in the presence of a catalyst, so as to obtain an esterified product. Next, the esterified product was subjected to cooling, removal of the catalyst and unreacted neopentanoic acid, decolorization, and deodorization in sequence, so as to obtain a carboxylate compound of formula (I-3).

Example 1

11.5 g of the carboxylate compound of formula (I-1) prepared in Synthesis Example 1, 3.5 g of an emulsifier (BASF Co., Ltd., Cat. No. Emulgade® 1000 NI), and 86 g of water were mixed homogeneously, so as to obtain a scalp protection composition of Example 1.

Comparative Example 1

2-octyldodecyl isostearate (CAS No. 93803-87-3) purchased from Patech Fine Chemicals Co., Ltd. (Cat. No. Paester™ ODIS) was used as a test sample of Comparative Example 1.

Comparative Example 2

Caprylic/capric triglyceride purchased from Patech Fine Chemicals Co., Ltd. (Cat. No. Paester™ GTCC) was used as a test sample of Comparative Example 2.

Comparative Example 3

Mineral oil was used as a test sample of Comparative Example 3.

Property Evaluation:

A. Hydrolysis Resistance 10 g of the carboxylate compound of formula (I-1) prepared in Synthesis Example 1 was mixed with 20 g of an alkaline aqueous solution with a pH value of 13 (which contained sodium hydroxide and water), and then subjected to a reaction at 40±1° C. for 4 hours. Next, the variation in acid value (mg KOH/g) was measured at the $0.75^{th}$, $2^{nd}$, $3^{rd}$, and $4^{th}$ hours after starting the reaction.

The carboxylate compound of formula (I-2) prepared in Synthesis Example 2, the carboxylate compound of formula (I-3) prepared in Synthesis Example 3, and the test samples of Comparative Examples 1 to 2 were subjected to the same reaction and measurement as described above.

The results are shown in Table 1 below. The smaller the variation in acid value, the better the hydrolysis resistance to strong bases is.

B. Spreadability

50 μL of the carboxylate compound of formula (I-1) prepared in Synthesis Example 1 was dropped on the center of a quantitative filter paper (NO. 5C), and after 5 minutes, the spreading area of the carboxylate compound of formula (I-1) on the quantitative filter paper was measured. The spreading rate ($mm^2$/min) was calculated by dividing the spreading area by the spreading time (i.e., 5 minutes).

The carboxylate compound of formula (I-2) prepared in Synthesis Example 2, the carboxylate compound of formula (I-3) prepared in Synthesis Example 3, and the test samples of Comparative Examples 1 to 3 were subjected to the same measurement as described above.

The results are shown in Table 1 below. The higher the spreading rate, the better the spreadability is.

C. Moisture Retention 0.1 g of the scalp protection composition of Example 1 was applied to the skin of a test subject. At the $1^{st}$, $2^{nd}$, and $3^{rd}$ hours after start of application of the scalp protection composition of Example 1, the skin moisture content (%) of the test subject was measured by using a skin moisture tester (Manufacturer: Cortex Technology; Model no.: DermaLab® Combo) under a temperature of 20° C.±3° C. and a relative humidity of 30%±5%.

The test samples of Comparative Examples 1 and 3 were subjected to the same measurement as described above.

The results are shown in Table 2 below. The higher the skin moisture content, the better the moisture retention is.

Results:

The results in Table 1 show that the variation in acid value determined for the carboxylate compounds of Synthesis Example 1 to 3 were lower than those determined for the test samples of Comparative Examples 1 and 2, indicating that the scalp protection composition containing the carboxylate compound of formula (I) has excellent hydrolysis resistance to strong alkaline hair products (i.e., hair dyes and perm agents).

In addition, the results in Table 1 show that the spreading rates determined for the carboxylate compounds of Synthesis Example 1 and 3 were higher than those determined for the test samples of Comparative Examples 1 to 3, and the spreading rate determined for the carboxylate compound of Synthesis Example 2 was higher than that determined for the test sample of Comparative Example 3. These results indicate that the scalp protection composition containing the carboxylate compound of formula (I) has an excellent spreadability, and hence can be easily and uniformly coated on the scalp.

Moreover, the result in Table 2 shows that at the $1^{st}$, $2^{nd}$, and $3^{rd}$ hours after start of application of the test sample, the skin moisture contents determined for the scalp protection composition of Example 1 were higher than those determined for the test samples of Comparative Examples 1 and 3. This result indicates that the scalp protection composition containing the carboxylate compound of formula (I) has excellent moisture retention.

TABLE 1

| Test sample | Variation in acid value (mg KOH/g) | | | | Spreading rate ($mm^2$/min) |
| --- | --- | --- | --- | --- | --- |
| | $0.75^{th}$ hour | $2^{nd}$ hour | $3^{rd}$ hour | $4^{th}$ hour | |
| Synthesis Example 1 (carboxylate compound of formula (I-1)) | <0.1 | <0.1 | 0.12 | 0.16 | 202 |
| Synthesis Example 2 (carboxylate compound of formula (I-2)) | <0.1 | <0.1 | <0.1 | <0.1 | 150 |
| Synthesis Example 3 (carboxylate compound of formula (I-3)) | <0.1 | <0.1 | <0.1 | <0.1 | 311 |
| Comparative Example 1 (2-octyldodecyl isostearate) | 0.21 | 0.26 | 0.28 | 0.32 | 150 |
| Comparative Example 2 (caprylic/capric triglyceride) | 2.6 | 5.6 | 7.1 | 8.2 | 169 |
| Comparative Example 3 (mineral oil) | Not determined | Not determined | Mot determined | Not determined | 80 |

TABLE 2

| Test sample | Skin moisture content (%) | | |
| --- | --- | --- | --- |
| | $1^{st}$ hour | $2^{nd}$ hour | $3^{rd}$ hour |
| Scalp protection composition of Example 1 (containing carboxylate compound of formula (I-1)) | 36.8 | 33.7 | 34.3 |

TABLE 2-continued

| | Skin moisture content (%) | | |
|---|---|---|---|
| Test sample | $1^{st}$ hour | $2^{nd}$ hour | $3^{rd}$ hour |
| Comparative Example 1 (2-octyldodecyl isostearate) | 28.0 | 22.7 | 19.3 |
| Comparative Example 3 (mineral oil) | 25.5 | 18.0 | 13.3 |

Summarizing the above test results, it is clear that the scalp protection composition of the present disclosure has excellent hydrolysis resistance, moisture retention, and spreadability. Therefore, applying the scalp protection composition on the scalp before dyeing or perming can effectively prevent the alkaline hair products (i.e., hair dyes and perm agents) from directly contacting the scalp, thereby protecting the scalp from being damaged by the alkaline hair products.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A scalp protection composition, comprising a carboxylate compound, an emulsifier, and water,
wherein the carboxylate compound is
a compound represented by formula (I-2):

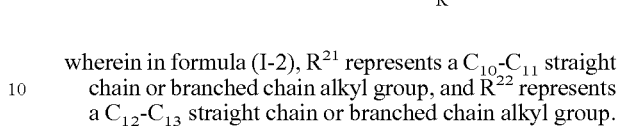

wherein in formula (I-2), $R^{21}$ represents a $C_{10}$-$C_{11}$ straight chain or branched chain alkyl group, and $R^{22}$ represents a $C_{12}$-$C_{13}$ straight chain or branched chain alkyl group.

2. The scalp protection composition according to claim 1, wherein the emulsifier is selected from the group consisting of fatty acid salt, sulfonate, amino acid salt, alkyl ether sulfate, alkyl sulfonate, sucrose ester, alkyl polyglucoside, glycerol ester, polyglycerol ester, sorbitan ester, polysorbate, fatty acid diethanolamide, fatty alcohol polyoxyethylene ether, fatty alcohol polyalkylene glycol ether, alkyl amide betaine, alkyl betaine, alkyl ammonium chloride, and combinations thereof.

3. The scalp protection composition according to claim 1, wherein the carboxylate compound is present in an amount ranging from 0.5 wt % to 99 wt %, based on the total weight of the scalp protection composition.

4. The method scalp protection composition according to claim 1, wherein the emulsifier is present in an amount ranging from 0.5 wt % to 50 wt %, based on the total weight of the scalp protection composition.

5. The scalp protection composition according to claim 1, wherein the water is present in an amount ranging from 0.5 wt % to 99 wt %, based on the total weight of the scalp protection composition.

* * * * *